United States Patent
Ragg (10) Patent No.: US 10,806,632 B2
(45) Date of Patent: Oct. 20, 2020

(54) ADHESIVE PATCH OR BANDAGE FOR USE IN TREATING BLOOD VESSEL DISEASES

(75) Inventor: Johann Christof Ragg, Berlin (DE)

(73) Assignee: Angioclinic AG, Frauenfeld (CH)

( * ) Notice: Subject to any disclaimer, the term of this patent is extended or adjusted under 35 U.S.C. 154(b) by 269 days.

(21) Appl. No.: 14/124,616

(22) PCT Filed: Jun. 8, 2012

(86) PCT No.: PCT/EP2012/060928
§ 371 (c)(1),
(2), (4) Date: Feb. 24, 2014

(87) PCT Pub. No.: WO2012/168449
PCT Pub. Date: Dec. 13, 2012

(65) Prior Publication Data
US 2014/0163606 A1 Jun. 12, 2014

(30) Foreign Application Priority Data
Jun. 9, 2011 (EP) .................................... 11169364

(51) Int. Cl.
*A61F 13/02* (2006.01)
*A61F 13/08* (2006.01)
(Continued)

(52) U.S. Cl.
CPC ...... *A61F 13/0243* (2013.01); *A61B 17/0057* (2013.01); *A61F 13/023* (2013.01);
(Continued)

(58) Field of Classification Search
CPC .......... C08L 83/04; A61L 15/58; A61L 15/44; A61F 13/02; A61F 13/0276;
(Continued)

(56) References Cited

U.S. PATENT DOCUMENTS 2,646,797 A 7/1953 Scholl
5,891,074 A * 4/1999 Cesarczyk .......... A61F 13/0203
128/109.1
(Continued)

FOREIGN PATENT DOCUMENTS

FR 2 447 713 8/1980
FR 2 460 130 1/1981
(Continued)

OTHER PUBLICATIONS

WO2010/037922A1_translation.PDF: english language machine translation of foreign reference doc WO2010037922A1.*
(Continued)

*Primary Examiner* — Anna K Kinsaul
*Assistant Examiner* — Caitlin A Carreiro
(74) *Attorney, Agent, or Firm* — Ballard Spahr LLP (57) ABSTRACT

An enhanced adhesive bandage sandwich (FIG. 1) for compressing blood vessels and a kit for assembling said bandage sandwich. A bandage or kit can be used as a medicament, particularly, for use in treating varicose veins. A bandage sandwich or kit can be used to compress veins or arteries. A method to produce said bandage sandwich can include providing a first adhesive bandage layer; applying an elastic body to the first adhesive bandage layer; and applying a second adhesive bandage layer to the first bandage layer. The elastic body of the bandage sandwich can be shaped to follow the contours of veins or arteries to be compressed.

19 Claims, 2 Drawing Sheets

(51) Int. Cl.
*A61B 17/00* (2006.01)
*A61F 13/00* (2006.01)
*A61B 17/12* (2006.01)

(52) U.S. Cl.
CPC ...... *A61F 13/0253* (2013.01); *A61F 13/0256* (2013.01); *A61F 13/08* (2013.01); *A61B 17/12009* (2013.01); *A61B 2017/00526* (2013.01); *A61F 2013/0028* (2013.01); *A61F 2013/00182* (2013.01); *A61F 2013/00468* (2013.01); *A61F 2013/00553* (2013.01); *A61F 2013/00578* (2013.01); *A61F 2013/00846* (2013.01)

(58) Field of Classification Search
CPC ........ A61F 13/0253; A61F 2013/00604; A61F 2013/00846; A61F 13/0243; A61F 13/023; A61F 13/0256; A61F 13/08; A61F 2013/00182; A61F 2013/00468; A61F 2013/00553; A61F 2013/00578; A61B 17/0057; A61B 17/12009; A61B 2917/00526
USPC ........ 602/41–49, 54; 606/201, 204; 424/445
See application file for complete search history.

(56) References Cited

U.S. PATENT DOCUMENTS

| | | | |
|---|---|---|---|
| 6,316,686 B1 | 11/2001 | Byrd | |
| 2004/0092999 A1* | 5/2004 | Lojewski | A61B 17/1325 606/185 |
| 2004/0127829 A1* | 7/2004 | Sigurjonsson | A61F 13/0203 602/41 |
| 2009/0308764 A1* | 12/2009 | Lee | A61F 15/001 206/219 |
| 2010/0266794 A1* | 10/2010 | Wright | A61L 15/60 428/35.7 |
| 2011/0125158 A1* | 5/2011 | Diwan | A61F 2/441 606/93 |

FOREIGN PATENT DOCUMENTS

| | | | |
|---|---|---|---|
| FR | 2 865 295 | 11/2006 | |
| FR | 2885295 A1 * | 11/2006 | ............. A61F 13/08 |
| FR | 2 936 408 | 4/2010 | |
| WO | WO 86/07252 | 12/1986 | |
| WO | WO 2006/053920 | 5/2006 | |
| WO | WO 2010037922 A1 * | 4/2010 | ........ A61M 25/0637 |
| WO | WO-2010037922 A1 * | 4/2010 | ........... A61F 13/023 |

OTHER PUBLICATIONS

WO2010037922A1_translation.PDF.*
Thomas ("Silicone Adhesives in Healthcare Applications"); Jan. 16, 2005—www.dowcorning.com.*
MatWeb Material Property Data—"Overview of Materials for Silicone Rubber".*
Shin-Etsu—"Silicone Rubber—Performance Test Results". PDF.*
Google search PDF showing online publication date of Shin-Etsu document.*
Thomas; "Silicone Adhesives in Healthcare Applications".*
Shin-Etsu: "Silicone Rubber—Performance Test Results".*
Thomas ("Silicone Adhesives in Healthcare Applications") (Year: 2005).*
Shin-Etsu ("Silicone Rubber—Performance Test Results") (Year: 2004).*
MatWeb Material Property Data—"Overview of Materials for Silicone Rubber" ( ) (Year: 0000).*
Grandidier (FR2885295) machine translation documents: description and claims (Year: 2006).*
International Search Report dated Aug. 6, 2012 in International Patent Application No. PCT/EP2012/060928.

* cited by examiner

ADHESIVE PATCH OR BANDAGE FOR USE IN TREATING BLOOD VESSEL DISEASES

This application is a U.S. National Stage Application of PCT International Patent Application No. PCT/EP2012/060928, which was filed on Jun. 8, 2012 and claims priority to European Patent Application No. 11169364.4, which was filed Jun. 9, 2011, the disclosure of each of which is incorporated herein by reference in its entirety.

FIELD OF THE INVENTION

The present invention is in the field of medicine, more in particular in the field of vein and arterial diseases such as aneurysms or dilatations in humans and animals. The invention is also in the field of pharmaceuticals/medical devices for treating such diseases.

BACKGROUND

In humans, there are various kinds of blood vessels. They are roughly grouped as arterial and venous, determined by whether the blood in it is flowing away from (arterial) or toward (venous) the heart. The term "arterial blood" is nevertheless used to indicate blood high in oxygen, with the exceptions of the pulmonary artery carrying "venous blood", and blood flowing in the pulmonary vein is rich in oxygen.

Pathological cavities or dilatations, e.g. arterial aneurysms, varicose veins, venous ectasias, or vascular malformations are often associated with different complications, as the dilated vessel wall may be more fragile and risky for rupture, possibly leading to severe bleeding, or thrombosis, with the risk of permanent postthrombotic damage, or pulmonary embolism even associated with high mortality. Dilated veins often develop incompetence of the vein valves with consequent venous insufficiency, meaning a reversed flow direction. Venous insufficiency is, when untreated, a chronic disease with increasing congestions of blood and lymphatic fluid. The increased venous pressure and the accumulation of blood with low oxygen and low nutrients has serious implications, comprising pain, heaviness, inability to walk or stand for long hours, and even complications like dermatitis, skin ulcers especially near the ankle, usually referred to as venous ulcers, and even development of carcinoma or sarcoma in longstanding venous ulcers. Many malformations, like varicose veins or spider veins, have ugly aspects disclosing patients from activities like public swimming or wearing short trousers or skirts.

In the past, therapy of vascular aneurysms, dilatations or ectasias has been surgical in the first choice. However, vascular surgery is frequently accompanied by incidental damage of neighbouring nerves or lymphatic vessels, wounds and wound infections, septicaemia, necrosis, even tissue loss or loss of the extremity. Also, intra- or postoperative bleedings may be serious. Surgery frequently requires general anaesthesia with several, partially serious adverse effects, i.e. intolerance of the patient for narcotic drugs, or hypoxia.

As an alternative to surgical removal, several methods of interventional treatment using thermal, thermo-optical, or mechanical means mediated by catheters have been developed, like laser beams operating via glass fibers at 810-1470 nm, radiofrequency probes, or steam-releasing tubes. A further, even more widely used sclerotherapy is the sclerotherapy via the injection of liquid sclerosant drugs. Known liquid sclerosant drugs are e.g. alcohols with detergent properties like polidocanol or sodium tetradecyl sulphate.

The liquid sclerosant drug is injected into the vessels. In order to circumvent some drawbacks of the liquid sclerosant drugs like missing imaging and dosage control, it has been established to produce a sclerosant drug foam by mixing the liquid sclerosant drug with a gas, obtaining a substance well distinguishable from blood in ultrasound images. For foaming the sclerosant drug (Sodium Tetradecyl Sulfate or polidocanol) is mixed with sterile air or a physiological gas (carbon dioxide) in syringes, by using mechanical pumps or by gas pressure. Foaming increases the surface area of the drug. The foam will adhere to the vessel wall and the contact will be more intense than by a fluid bolus quickly passing by. Therefore, sclerosant drug foam is more efficacious in causing sclerosis than the liquid sclerosant drug (thickening of the vessel wall and sealing off the blood flow; Yamaki T, Nozaki M, Iwasaka S (2004). "Comparative study of duplex-guided foam sclerotherapy and duplex-guided liquid sclerotherapy for the treatment of superficial venous insufficiency". Dermatol Surg 30 (5): 718-22).

All these methods aim at denaturing functional proteins of the innermost vessel layer (intima) with the consequence of local blood platelet aggregation, subsequent thrombotic closure, organization and gradual transformation to connective tissue.

The more the aneurysm or dilatation causes symptoms or cosmetic defects, in addition to a mere occlusion, shrinkage is required. Some modalities like endovenous laser, radiofrequency, or steam vein sclerosis may induce some shrinkage, but it will be incomplete or unstable as an energy required to sufficiently shrink the muscular layer would seriously co-affect the nerve-containing outer adventitia layer or even neighbouring nerves, and cause serious pain. Sclerotherapy using chemical agents is also insufficient in generating lasting diameter reductions: The agents will initially induce a spasm which reduces the vessels diameter, but as the fluid or foam-like agent will be washed off within seconds or minutes, and the spasm will decrease rapidly. Sclerosant drug foams will float on blood and partially not reach the whole circumference of the lumen. Furthermore, sclerosant drug foams will disintegrate rapidly within vessels. The consequence is blood re-entry and partial re-sizing of the treated vessel. The larger the blood volume contained within the treated structure, the higher the frequency of painful inflammatory resorptive reactions which may require surgical or interventional thrombus removal and/or anti-inflammatory drugs and painkillers for relief.

Many vascular treatments include principles of compression. This is in particular true for venous treatments—surgical, interventional, or conservative. In the conservative treatment of venous insufficiency, external pressure is applied by medical compression stockings or bandages. The purpose is to counteract the increased pressure in veins and tissue. Furthermore, the diameter of dilated veins may be reduced and minor degrees of insufficiency may be reversed, as long as the pressure is maintained. The pressure mediated by stockings or bandages is concentric.

After surgical treatment, compression strategies follow quite other aims: First, to avoid bleeding from cuts and spots where vessels or tissue have been ripped off. Second, the decrease of vessel diameters will increase the flow velocity and thus prevent thrombosis. This is in particular relevant in vein disease. An additional benefit is the prevention of posttraumatic swelling. Although surgery is always related to certain spots or diseased vessel segments, compression is generally applied in a concentric way which limits the applicable pressure by relevant pain sensations. It would be desirable to apply pressure mainly on the treated locations.

In interventional treatments, there are neither cuts nor tissue damage requiring compression. General anaesthesia is typically not needed, so patients are capable to move during and after the treatments. Therefore, there is no particular risk of thrombosis, and no compression required for prevention. However, in contrary to surgery, the diseased vessels are not removed but still in place. As all known interventional treatments are not able to induce an immediate, total and permanent lumen shrinkage, focal compression could help to accelerate the gradual shrinkage process by blood clot organisation and transfer to connective tissue.

After treatment compression stockings provide graduated pressure on the structures treated. Unlike traditional dress or athletic stockings and socks, compression stockings use stronger elastics to create significant pressure on the legs, ankles and feet. Long stretch compression bandages have long stretch properties, meaning their high compressive power can be easily adjusted. However, they also have a higher resting pressure and usually are removed at night WO 2004/112666 discloses a bandage with an elastic compression means. This however reversibly changes its shape which is a drawback. Here, the disclosure relates to a dressing comprising a swab that can be placed against the wound and absorbs secretion there from, a means for pressing the swab against a wound, and a fastening means for locally fixing the dressing. The pressing means is embodied as an open-pore or closed-pore foam material which can be deformed in an elastically reversible and delayed manner and is accommodated within the dressing between the swab and an outer cover layer that overlaps the swab.

After interventional vessel therapy or sclerosant drug foam treatment it would be advantageous to have a means of applying pressure directed to the treated vessels, It should be avoided to apply pressure on healthy tissue as this may generate pain or even tissue damage. The pressure in the whole extremity should in general not be increased, except in cases with indication like deep vein insufficiency or postthrombotic syndrome There are several disadvantages of common compression media: Stockings of adequate pressure are difficult to put on, and many patients will not be able to accomplish this without a helping hand. Bandages, on the other hand, are easy but time-consuming in their application, and the pressure depends very much on the tension applied during binding and may easily be too soft or too hard. Stockings, less frequently also bandages, may cause allergic reactions. Both will remove fluid and fat from the skin and make it more fragile to lesions, inflammations or infections. The comfort of compression stockings, trousers or bandages is low (pain by pressure, displacement) and the patient compliance is poor To apply focal transcutaneous pressure on vessel structures, several materials like dentist's rolls, tissue rolls, rubber foam or plastic foam have been used. They all require bandages or tapes for fixation. Often, the focal pressure is too high with the consequence of skin lesions, in particular in joint regions where every step will induce sheer forces to the skin.

Blood vessels and in particular varicose veins have a multitude of forms and sizes, often highly tortuous, or branched.

Thus, the present invention solves the problem by providing for an adhesive patch or bandage and a kit for producing said patch.

It has also been shown that compression reduces the intensity of postoperative pain after, e.g. endovenous laser ablation; see Lugli et al., Phlebology 2009, 24:151-156.

Compression after sclerotherapy is described as it leads to better results; see Weiss et al., Dermatological Surgery 1999; 25:105-108 and see Noppeney et al., Phlebologie 1/2011.

SUMMARY OF THE INVENTION

The present invention relates to an adhesive bandage sandwich for compressing blood vessels and a kit for assembling said bandage sandwich. Moreover, the invention relates to a bandage or kit for use as a medicament, particularly, for use in treating varicose veins. The invention also relates to the use of a bandage sandwich or kit for compressing veins or arteries and a method to produce said bandage sandwich. Furthermore, the invention relates to a bandage sandwich obtainable by the inventive method.

The present invention relates to an adhesive bandage sandwich for compressing veins or arteries, comprising the following layers: (i) a first adhesive bandage layer [1], adapted to adhere to human skin and which is substantially see-through, (ii) an elastic body [3] which is form stable and preferably a silicone rubber, wherein the elastic body may have varying shapes depending on the vein or artery to be compressed, (iii) a second adhesive bandage layer [2], adapted to adhere to said first adhesive bandage layer.

The invention also relates to a kit for producing an adhesive bandage for compressing veins or arteries, comprising (i) a first adhesive bandage [1], adapted to adhere to human skin, which is substantially see-through, (ii) a container with a gel or paste precursor which after hardening forms elastic body [3] which is form stable and preferably a silicone rubber, wherein the elastic body may have varying shapes depending on the vein or artery to be compressed, wherein the precursor hardens or cures within between 1 min and 10 hours once it contacts atmospheric air, and (iii) a second adhesive bandage [2], adapted to adhere to said first adhesive bandage.

The invention also relates to the inventive bandage sandwich or kit for use as a medicament.

The invention further relates to the use of the inventive bandage sandwich or kit for compressing veins or arteries.

The invention also relates to a method for producing a bandage sandwich for compressing veins or arteries comprising the steps of (i) providing a first adhesive bandage layer [1]; (ii) applying an elastic body [3] to the first bandage layer [1], wherein the elastic body [3] is shaped to follow the contours of the veins or arteries to be compressed; (iii) applying a second adhesive bandage layer [2] to the first adhesive bandage layer [1], wherein the elastic body [3] is embedded and fixed within said layers.

The invention also relates to a bandage sandwich obtainable by the inventive method.

DETAILED DESCRIPTION OF THE INVENTION

The present invention relates to an adhesive bandage sandwich for compressing veins or arteries, comprising the following layers: (i) a first adhesive bandage layer [1], adapted to adhere to human skin and which is substantially see-through, (ii) an elastic body [3] which is form stable and preferably a silicone rubber, wherein the elastic body may have varying shapes depending on the vein or artery to be compressed, (iii) a second adhesive bandage layer [2], adapted to adhere to said first adhesive bandage layer.

The bandage sandwich should be non-toxic, biocompatible and, preferably, biodegradable, which is particularly true for that side of the first adhesive layer, which is intended to be in contact with the skin. The first adhesive bandage layer can further comprise a superabsorbent polymer which can absorb blood. This layer can also comprise additives, e.g. a haemostatic compound to induce blood clotting or antimicrobial properties to promote wound healing. Preferably, this layer is sterile. More preferably, the whole bandage sandwich is sterile and packaged.

The bandage sandwich is preferably compatible with ultrasonic devices.

In one embodiment, the first bandage layer is elastomeric. In a further embodiment, the second bandage layer is also elastomeric. It is desired that the bandage layers are made of breathable films or perforated. It is also desired that the bandage layers are stretchable to a certain degree in order to fit the anatomy of the body.

In another embodiment, the side of the first bandage layer is coated with a suitable skin-friendly adhesive. If it is desired the first bandage layer is not coated with an adhesive. Then, the bandage sandwich is attached to the skin by another adhesive tape or bandage.

The second bandage layer sticks to the first bandage layer. In between the first and the second bandage layers lies the elastic body and is fixed in its mobility by the adhesive forces of the two bandage layers. The bandage sandwich can be adhered to the skin and allows for developing a compression force to the vein or artery to be compressed. The skilled person knows how to chose and vary the compression force.

The elastic body of the bandage sandwich may have different shapes. For example, the elastic body can be long, short, thick, thin, straight, curved, sigmoid, angled and combinations thereof. Preferred shapes are natural occurring shapes which have been mimicked from the contours of veins and arteries of human bodies. Preferably, a variety of adhesive bandage sandwich candidates with different shapes are provided. From these candidates the matching bandage sandwich can be selected by comparing the contour of the artery or vein to be compressed with the bandage sandwich types available.

One advantage of the present invention is that it enables a target specific compression of the blood vessels to be compressed, i.e. specific compression of the blood vessels to be compressed, whereas the surrounding area is not or not very much compressed. Another advantage is that the elastic body is form stable, but elastic. Therefore a long-lasting compression force is guaranteed without loosing the comfort of an elastic material. Particularly, shear forces on the skin can be prevented which can appear especially in joint regions. The present invention is particular useful for compressing large blood vessels which cannot be sufficiently enabled with current bandages.

In one embodiment the second adhesive layer is also substantially see-through.

The advantage of a see-through bandage layer is that it enables the attachment of the bandage sandwich precisely onto the blood vessel to be compressed and the evaluation of the correct fit after attachment.

Suitable materials are silicones. More precisely called polymerized siloxanes or polysiloxanes, silicones are mixed inorganic-organic polymers with the chemical formula [R2SiO]n, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate.

In some cases organic side groups can be used to link two or more of these —Si—O— backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Silicone rubber is a rubber-like material composed of silicone—itself a polymer—containing silicon together with carbon, hydrogen, and oxygen. Silicone rubbers are widely used in industry, and there are multiple formulations. Silicone rubbers are often one- or two-part polymers, and may contain fillers to improve properties or reduce cost. Silicone rubber is generally non-reactive, stable, and resistant to extreme environments and temperatures from −55° C. to +300° C. while still maintaining its useful properties. Due to these properties and its ease of manufacturing and shaping, silicone rubber can be found in a wide variety of products, including: automotive applications; cooking, baking, and food storage products; apparel such as undergarments, sportswear, and footwear; electronics; medical devices and implants; and in home repair and hardware with products such as silicone sealants.

During manufacture heat may be required to vulcanize (set or cure) the silicone into its rubber-like form. This is normally carried out in a two stage process at the point of manufacture into the desired shape, and then in a prolonged post-cure process. It can also be injection molded. Herein, it is preferred if the silicone rubber is water based and when the water evaporates the rubber becomes hard.

(Shore) Durometer is one of several measures of the hardness of a material. Hardness may be defined as a material's resistance to permanent indentation. The durometer scale was defined by Albert F. Shore, who developed a measurement device called a durometer in the 1920s. The term durometer is often used to refer to the measurement, as well as the instrument itself. Durometer is a dimensionless quantity and typically used as a measure of hardness in polymers, elastomers and rubbers. The procedure of determination is laid down in DIN norm 53505. An overview of different materials along with its durometer values are given in Table 1.

TABLE 1

Typical durometer values of some materials.

| Material | Durometer |
|---|---|
| Bicycle gel seat | 15-30 |
| Chewing gum | 20 |
| Sorbothane | 40 |
| Sorbothane | 30-70 |
| Rubber band | 25 |
| Door seal | 55 |
| Automotive tire tread | 70 |
| Soft skateboard wheel | 75 |
| Hydraulic O-ring | 70-90 |
| Hard skateboard wheel | 98 |
| Ebonite Rubber | 100 |
| Solid truck tires | 50 |
| Hard hat | 75 |

In another embodiment the elastic body [2] is a silicone rubber with a shore value of between 15 and 60 when measured according to DIN 53505.

In yet another embodiment the elastic body is a silicone rubber with a shore value of between 40 and 60 when measured according to DIN 53505.

In yet another embodiment the elastic body has at least one feature selected from the group of:

| | |
|---|---|
| Raw density [g/cm$^3$] | 0.7-1.2 |
| Shore value (DIN 53505) | 5-25 |
| Elastic modulus [N/mm$^2$] | 0.1-0.6 |
| Tensile strength [%] | 100-600 |
| Resilience [%] | >50 |
| Practical acceptance of motion [%] | 10-40 |
| Elongation at break [n/mm$^2$] | 0.2-1.4 |

Preferably, the elastic body has at least two feature selected from the table above. For example, the elastic body has a density and a shore value as given above. Alternatively, the elastic body has at least three, four, five, six or all seven features selected from the table above. This means, the elastic body has a density and/or a shore value and/or an elastic modulus as given above. Alternatively, the elastic body has a density and/or a shore value and/or an elastic modulus and/or a tensile strength as given above. Alternatively, the elastic body has a density and/or a shore value and/or an elastic modulus and/or a tensile strength and/or a resilience as given above. Alternatively, the elastic body has a density and/or a shore value and/or an elastic modulus and/or a tensile strength and/or resilience and/or a practical acceptance of motion as given above. Alternatively, the elastic body has a density and/or a shore value and/or an elastic modulus and/or a tensile strength and/or resilience and/or a practical acceptance of motion and/or an elongation at break as given above. Preferably, the elastic body is of silicone.

In a preferred embodiment the elastic body has at least one feature selected from the group of:

| | |
|---|---|
| Raw density [g/cm$^3$] | 0.8-1.1 |
| Shore value (DIN 53505) | 7.5-20 |
| Elastic modulus [N/mm$^2$] | 0.2-0.5 |
| Tensile strength [%] | 200-500 |
| Resilience [%] | >75 |
| Practical acceptance of motion [%] | 15-30 |
| Elongation at break [n/mm$^2$] | 0.4-1.2 |

Preferably, the elastic body has at least two feature selected from the table above. For example, the elastic body has a density and a shore value as given above. Alternatively, the elastic body has at least three, four, five, six or all seven features selected from the table above. This means, the elastic body has a density and/or a shore value and/or an elastic modulus as given above. Alternatively, the elastic body has a density and/or a shore value and/or an elastic modulus and/or a tensile strength as given above. Alternatively, the elastic body has a density and/or a shore value and/or an elastic modulus and/or a tensile strength and/or a resilience as given above. Alternatively, the elastic body has a density and/or a shore value and/or an elastic modulus and/or a tensile strength and/or resilience and/or a practical acceptance of motion as given above. Alternatively, the elastic body has a density and/or a shore value and/or an elastic modulus and/or a tensile strength and/or resilience and/or a practical acceptance of motion and/or an elongation at break as given above. Preferably, the elastic body is of silicone.

In a more preferred embodiment the elastic body has at least one feature selected from the group of:

| | |
|---|---|
| Raw density [g/cm$^3$] | 0.9-1.0 |
| Shore value (DIN 53505) | 10-15 |
| Elastic modulus [N/mm$^2$] | 0.3-0.4 |
| Tensile strength [%] | 300-400 |
| Resilience [%] | >90 |
| Practical acceptance of motion [%] | 20-25 |
| Elongation at break [n/mm$^2$] | 0.5-1.0 |

Preferably, the elastic body has at least two feature selected from the table above. For example, the elastic body has a density and a shore value as given above. Alternatively, the elastic body has at least three, four, five, six or all seven features selected from the table above. This means, the elastic body has a density and/or a shore value and/or an elastic modulus as given above. Alternatively, the elastic body has a density and/or a shore value and/or an elastic modulus and/or a tensile strength as given above. Alternatively, the elastic body has a density and/or a shore value and/or an elastic modulus and/or a tensile strength and/or a resilience as given above. Alternatively, the elastic body has a density and/or a shore value and/or an elastic modulus and/or a tensile strength and/or resilience and/or a practical acceptance of motion as given above. Alternatively, the elastic body has a density and/or a shore value and/or an elastic modulus and/or a tensile strength and/or resilience and/or a practical acceptance of motion and/or an elongation at break as given above. Preferably, the elastic body is of silicone.

In addition to the features mentioned above the elastic body has preferably at least one of the following features, too:

| | |
|---|---|
| Viscosity | Paste-like, steady |
| Mode of hardening | Neutral cross-linking |
| Duration of skin formation | 8-12 minutes (at 23° C. and 50% relative humidity) |
| Hardening (vulcanising) | 2 mm/24 h (at 23° C. and 50% relative humidity) |
| Temperature resistance [° C.] | 10-50 |
| Colour | Transparent |
| Thickness of application [mm] | 1-25 |
| Storability | 6-12 months in closed cartridges |
| Other | Hygienic pure |

Preferably, the elastic body has at least two features selected from the table above. Alternatively, the elastic body has at least three, four, five, six or all seven features selected from the table above. The features may be combined in any way as needed.

In a further embodiment the elastic body is a silicone rubber and the silicone rubber is a water based silicone rubber.

In a preferred embodiment the elastic body is a silicone rubber and the silicone rubber is for example 1-k-polysiloxane.

The form of the elastic body may be created, shaped and made by moving for example valves or syringes of different sites so as to adapt to the vein size and shape.

Ideally, preferably the elastic body is transparent for ultra sonic imaging.

Preferably, the first [1] and/or second adhesive layer [2] have a water vapour transmission rate of 1000 g/m2/24 hours, preferably 1200 g/m2/24 hours, even more preferably 2000 g/m2/24 hours when measured according to DIN EN 13726.

There are various techniques to measure moisture vapor transmission rate (MVTR), also called water vapor transmission rate (WVTR), ranging from gravimetric techniques that measure the gain or loss of moisture by mass, to highly sophisticated instrumental techniques that in some designs can measure extremely low transmission rates. Note that special care has to be taken in measuring porous substances such as fabrics as some techniques are not appropriate. Likewise for very low levels, many techniques would not have the resolution to provide a reliable result. Numerous standard methods are described in ISO, ASTM, BS, DIN etc.—these are quite often industry-specific. Instrument manufacturers will often be able to provide test methods developed to fully exploit the specific design which they are selling.

The condition under which the measurement is made has a considerable influence on the result. Both the temperature of and humidity gradient across the sample need to be measured, controlled and recorded with the result. An MVTR result without specifying these conditions is almost meaningless. Certainly no two results should be compared unless the conditions are known. The most common international unit for the MVTR is $g/m^2/day$. In the USA, $g/100\ in^2/day$ is also in use, which is approximately 1/15 of the value of $g/m^2/day$ units. (More precisely, the ratio is 1/15.500031, or very close to 2/31.) Typical rates in aluminium foil laminates may be as low as 0.001 $g/m^2/day$, whereas the rate in fabrics can measure up to several thousand $g/m^2/day$.

Often, testing is conducted on a sheet of material. Calculations based on that can be useful when designing completed structures (packages, clothing, etc). Seams and seals are also very important to end-use performance; performance verification and validation of complete containers or irregular objects is often recommended.

In a preferred embodiment, the first adhesive layer [1] is of a material selected from the group of polyurethane, polyether urethane, polyester urethane, polyether-polyamid-copolymers, polyacrylate, and the respective films thereof.

Ideally, the first [1] and/or second adhesive layer [2] has a thickness of between 15 μm and 50 μm, preferably between 20 μm and 40 μm and more preferably between 25 μm and 30 μm.

The first [1] and/or second adhesive layer [2] preferably comprises adhesive glue that is a water based acrylate.

An example of an adhesive layer is tegaderm from 3M.

The first [1] and/or second adhesive layer [2] preferably comprises 20 to 100 $g/m^2$ adhesive glue.

The invention also relates to a kit for producing an adhesive bandage for compressing veins or arteries, comprising (i) a first adhesive bandage [1], adapted to adhere to human skin, which is substantially see-through, (ii) a container with a gel or paste precursor which after hardening forms elastic body [3] which is form stable and preferably a silicone rubber, wherein the elastic body may have varying shapes depending on the vein or artery to be compressed, wherein the precursor hardens or cures within between 1 min and 10 hours once it contacts atmospheric air, and (iii) a second adhesive bandage [2], adapted to adhere to said first adhesive bandage.

As used herein, a kit is a packaged combination optionally including instructions for use of the combination and/or other reactions and components for such use.

Preferably, a variety of materials is provided having different shapes of the adhesive bandage layers and/or elastic body, so that the skilled person can chose the best one depending on the contour of the blood vessel to be compressed and/or the anatomy of the part of the body wherein said blood vessel lies. If a kit is used the skilled person can ideally chose from pre-formed bandage layer (e.g. big, small, rectangular, square, round) or, alternatively, cut tailored sheets. The same is true for the elastic body: it can be either chosen from pre-formed bodies or an elastic body is tailor-made from a precursor. The precursor comes ideally in a tube wherein the skilled person can easily make the desired shape by pressing the precursor directly onto the first layer.

The inventive kit is particular useful for large (30-120 cm) and/or twisty blood vessels. In this case, pre-formed elastic bodies are not suitable for a selective compression of large blood vessels. In contrast, the elastic body is tailor-made depending on the size and contour of the blood vessel to be compressed.

Preferably, also the second adhesive bandage of the inventive kit is substantially see-through.

Preferably, after hardening of the precursor of the inventive kit the elastic body has a shore value of between 15° and 60° when measured according to DIN 53505.

More preferably, after hardening of the precursor of the inventive kit the elastic body has a shore value of between 40° and 60° when measured according to DIN 53505.

The elastic body precursor of the inventive kit is preferably a silicone rubber and the silicone rubber is a water based silicone rubber.

The elastic body precursor of the inventive kit is preferably a silicone rubber and the silicone rubber is for example 1-k-polysiloxane.

The first [1] and/or second adhesive bandage [2] of the inventive kit has preferably a water vapour transmission rate of 1000 g/m2/24 hours, preferably 1200 g/m2/24 hours, even more preferably 2000 g/m2/24 hours when measured according to DIN EN 13726.

The first [1] and/or second adhesive bandage [2] of the inventive kit is preferably of a material selected from the group of polyurethane, polyether urethane, polyester urethane, polyether-polyamid-copolymers, polyacrylate, and the respective films thereof.

The first [1] and/or second adhesive bandage [2] of the inventive kit has preferably a thickness of between 15 μm and 50 μm.

The first [1] and/or second adhesive bandage [2] of the inventive kit comprises preferably adhesive glue which is a water-based acrylate glue.

The first [1] and/or second adhesive bandage [2] of the inventive kit comprises preferably 20 to 100 g/m2 adhesive glue.

The invention also relates to the inventive bandage sandwich or kit for use as a medicament.

Preferably, the inventive bandage sandwich or kit is for use in treating venal or arterial diseases.

Venal or arterial diseases can be arterial aneurysms, varicose veins, venous ectasias or vascular malformations.

More preferably, the inventive bandage sandwich or kit is for use in treating varicose veins.

Varicose veins are veins that have become enlarged and tortuous. The term commonly refers to the veins on the leg, although varicose veins can occur elsewhere. Varicose veins are most common in the superficial veins of the legs, which are subject to high pressure when standing. Besides cosmetic problems, varicose veins are often painful, especially when standing or walking. They often itch, and scratching them can cause ulcers. Serious complications are rare.

In another embodiment the inventive bandage sandwich or kit can be used for treating reticular veins (blue veins) and telangiectasias (spider veins), which also involve valvular insufficiency.

The inventive bandage sandwich or kit is particularly for use in treating venal or arterial diseases, wherein said disease requires compression of veins or arteries.

Examples for such diseases are arterial aneurysms, varicose veins, venous ectasias or vascular malformations.

The invention further relates to the use of the inventive bandage sandwich or kit for compressing veins or arteries.

The inventive bandage sandwich or kit can be also used for compressing veins or arteries in cosmetic treatments.

The invention also relates to a method for producing a bandage sandwich for compressing veins or arteries comprising the steps of (i) providing a first adhesive bandage layer [1]; (ii) applying an elastic body [3] to the first bandage layer [1], wherein the elastic body [3] is shaped to follow the contours of the veins or arteries to be compressed; (iii) applying a second adhesive bandage layer [2] to the first adhesive bandage layer [1], wherein the elastic body [3] is embedded and fixed within said layers.

In one embodiment the bandage sandwich is fully assembled on the skin: First, the first bandage layer is attached to the skin. Then, the elastic body precursor is added so that it follows the contours of the veins or arteries to be compressed. The thickness of the elastic body can be varied, e.g. to vary the compression force, as would be understood by the skilled person. After hardening of the precursor, the second bandage layer is adhered to the first one whereas the elastic body is embedded and fixed between the two layers.

Alternatively, the first bandage layer is put onto the skin not before the precursor has hardened and then further assembled on the skin.

If desired the contour of the veins or arteries to be compressed is copied onto the first bandage layer by putting it onto the skin and afterward removed from the skin. Then, the elastic body precursor is added onto the first bandage layer. After hardening the bandage is further assembled and placed back onto the skin or first placed on the skin and further assembled there.

Further combinations are obvious to the skilled person.

The invention also relates to a bandage sandwich obtainable by the inventive method.

FIGURE CAPTIONS

FIG. 3: a) before; b) with invention; c) after 10 days. The invention was present and used also during showering in a bath tub. Astonishingly, the vein's diameter is reduced by more than 20% when compared to a standard compression method.

Figure 1:
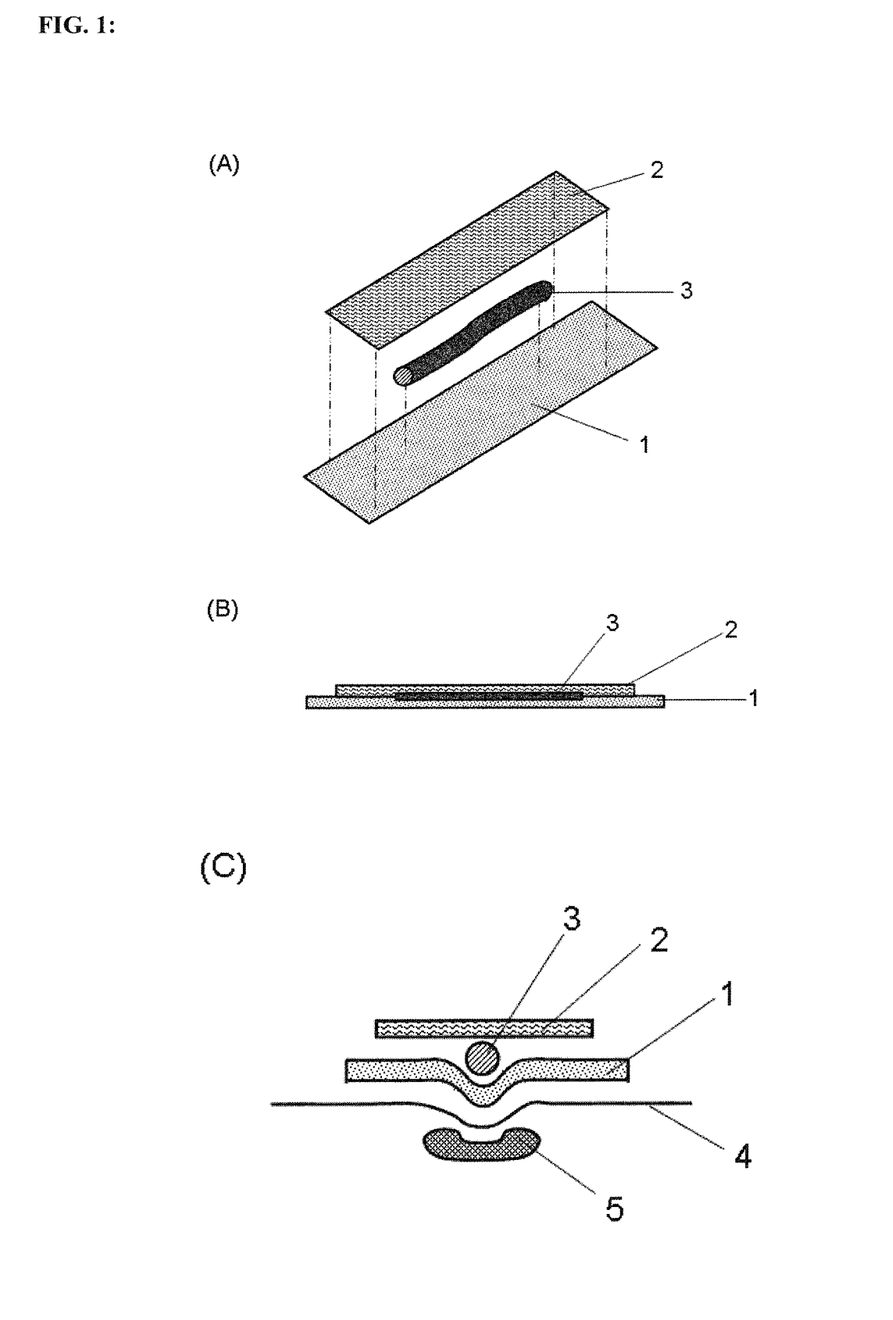
FIG. 1: Assembling of the inventive bandage sandwich in (A) exploded view; (B) side view; (C) side view (90° rotated): (1) first adhesive bandage layer; (2) second adhesive bandage layer; (3) elastic body; (4) skin; (5) blood vessel to be compressed.
Figure 2:
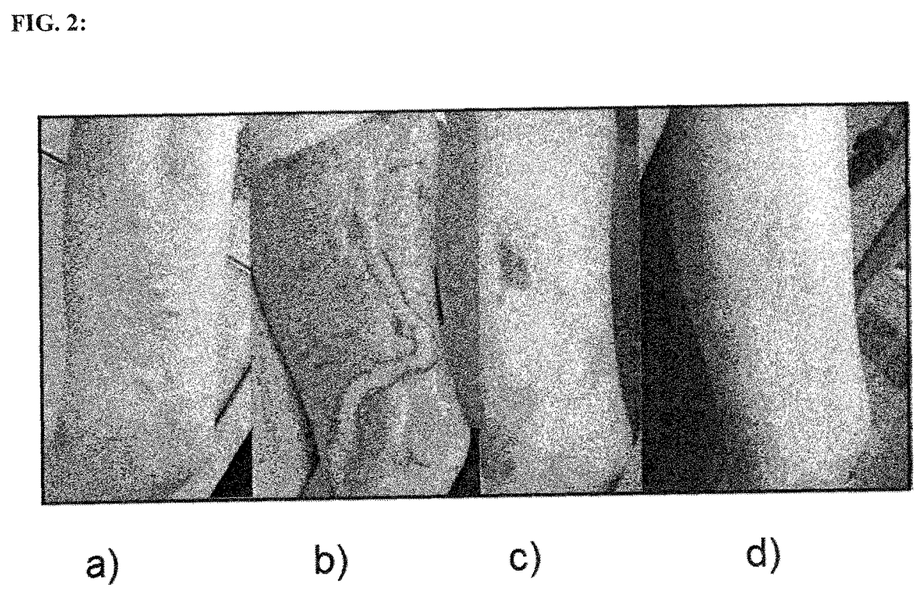
FIG. 2: a) before; b) with invention; c) 1 week; d) 3 weeks.
Figure 3:
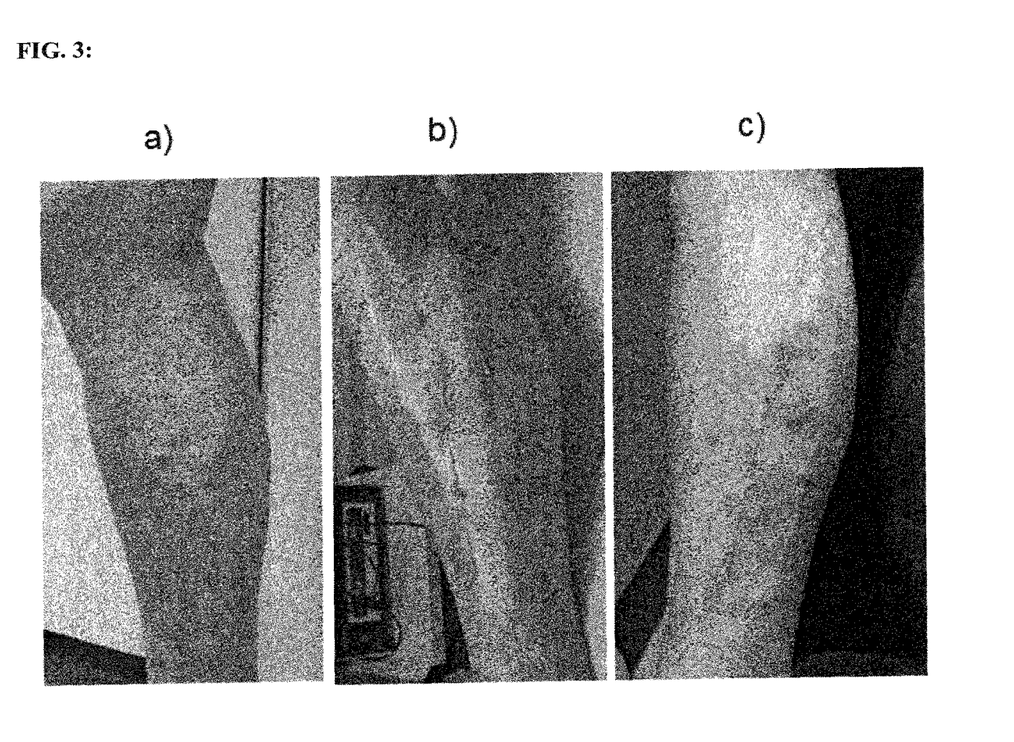

The invention claimed is:

1. An adhesive bandage sandwich for compressing veins or arteries, comprising the following layers:
   a. a first adhesive bandage layer (1), adapted to adhere to human skin,
   b. an elastic body (3) which is a form stable and hardened silicone rubber having a raw density between 0.8 and 1.1 g/cm$^3$,
   c. a second adhesive bandage layer (2),
   wherein, prior to hardening, the elastic body (3) is adapted to be applied to the first adhesive bandage layer and selectively shaped to follow the contours of the veins or arteries to be compressed,
   wherein the second adhesive bandage layer is adapted to adhere to said first adhesive bandage layer to embed and fix the elastic body within said first and second adhesive bandage layers,
   wherein the first adhesive bandage layer (1) is sufficiently see-through to permit evaluation of a location of the adhesive bandage sandwich relative to a vein or artery positioned underneath the adhesive bandage sandwich,
   wherein the first adhesive bandage layer, the elastic body, and the second adhesive bandage layer are adapted to be separately applied and fully assembled on the skin to form the adhesive bandage sandwich, and
   wherein at least one of the first adhesive bandage layer (1) or the second adhesive bandage layer (2) comprises 20 to 100 g/m$^2$ adhesive glue.

2. The adhesive bandage sandwich according to claim 1, wherein the elastic body has a shore value of between 5 and 25 when measured according to DIN 53505.

3. The adhesive bandage sandwich according to claim 2, wherein the elastic body has a shore value of between 7.5 and 20 when measured according to DIN 53505.

4. The adhesive bandage sandwich according to claim 1, wherein the second adhesive bandage layer is also sufficiently see-through to permit evaluation of a location of the adhesive bandage sandwich relative to a vein or artery positioned underneath the adhesive bandage sandwich.

5. The adhesive bandage sandwich according to claim 1, wherein the elastic body is a water based silicone rubber.

6. The adhesive bandage sandwich according to claim 1, wherein the silicone rubber of the elastic body is 1-k-polysiloxane.

7. The adhesive bandage sandwich according to claim 1, wherein at least one of the first (1) and second adhesive bandage layers (2) has a water vapour transmission rate of 1000 g/m2/24 hours, preferably 1200 g/m2/24 hours, even more preferably 2000 g/m2/24 hours when measured according to DIN EN 13726.

8. The adhesive bandage sandwich according to claim 1, wherein at least one of the first (1) and second adhesive bandage layers (2) is of a material selected from the group of polyurethane, polyether urethane, polyester urethane, polyether-polyamid-copolymers, polyacrylate, and the respective films thereof.

9. The adhesive bandage sandwich according to claim 1, wherein at least one of the first (1) and second adhesive bandage layers (2) has a thickness of between 15 μm and 50 μm.

10. The adhesive bandage sandwich according to claim 1, wherein at least one of the first (1) and second adhesive bandage layers (2) comprises adhesive glue which is a water based acrylate glue.

11. The adhesive bandage sandwich according to claim 1, wherein the elastic body has a practical acceptance of motion ranging from 10% to 40%.

12. The adhesive bandage sandwich according to claim 1, wherein the elastic body has an elastic modulus ranging from 0.1 to 0.6 N/mm$^2$.

13. The adhesive bandage sandwich according to claim 1, wherein the elastic body has a resilience greater than 50%.

14. The adhesive bandage sandwich according to claim 1, wherein the elastic body has a tensile strength at yield ranging from 0.2 to 1.4 n/mm$^2$.

15. A kit for producing an adhesive bandage for compressing veins or arteries, comprising:
- a. a first adhesive bandage layer (1), adapted to adhere to human skin,
- b. a container with a gel or paste precursor which after hardening forms an elastic body (3) which is form stable and a silicone rubber having a raw density between 0.8 and 1.1 g/cm$^3$, wherein the elastic body may have varying shapes depending on the vein or artery to be compressed, wherein the precursor hardens or cures within between 1 min and 10 hours once the precursor contacts atmospheric air, and
- c. a second adhesive bandage layer (2), wherein, prior to hardening, the elastic body (3) is adapted to be applied to the first adhesive bandage layer and selectively shaped to follow the contours of the veins or arteries to be compressed, wherein the second adhesive bandage layer is adapted to adhere to said first adhesive bandage layer to embed and fix the elastic body within said first and second adhesive bandage layers, wherein the first adhesive bandage layer is sufficiently see-through to permit evaluation of a location of the adhesive bandage relative to a vein or artery positioned underneath the adhesive bandage, wherein the first adhesive bandage layer, the elastic body, and the second adhesive bandage layer are adapted to be separately applied and fully assembled on the skin to form the adhesive bandage, and wherein at least one of the first adhesive bandage layer (1) or the second adhesive bandage layer (2) comprises 20 to 100 g/m$^2$ adhesive glue.

16. The kit according to claim 15, for use as a medicament.

17. Use of the kit according to claim 15, for compressing veins or arteries in cosmetic treatments.

18. A method for producing a bandage sandwich for compressing veins or arteries of a human or animal patient comprising the steps of:
- a. providing a first adhesive bandage layer (1);
- b. applying an elastic body (3) to the first bandage layer (1), wherein the elastic body (3) is a silicone rubber shaped to follow the contours of the veins or arteries to be compressed, wherein applying the elastic body to the first bandage layer comprises:
    applying a gel or paste precursor to the first bandage layer;
    selectively shaping the gel or paste precursor to follow the contours of the veins or arteries to be compressed; and
    allowing the gel or paste precursor to harden to form the elastic body;
- c. applying a second adhesive bandage layer (2) to the first adhesive bandage layer (1), wherein the elastic body (3) is embedded and fixed within said first and second adhesive bandage layers, wherein the bandage sandwich is fully assembled on skin of the human or animal patient.

19. A bandage sandwich obtainable by the method according to claim 18.

* * * * *